United States Patent [19]

Ranoux

[11] Patent Number: 5,532,155
[45] Date of Patent: Jul. 2, 1996

[54] SPONTANEOUS CYCLE FERTILIZATION METHOD

[76] Inventor: Claude Ranoux, 2 Beverly Rd., Arlington, Mass. 02174

[21] Appl. No.: 977,409
[22] PCT Filed: Jul. 1, 1992
[86] PCT No.: PCT/FR92/00615
  § 371 Date: Apr. 30, 1993
  § 102(e) Date: Apr. 30, 1993
[87] PCT Pub. No.: WO93/00863
  PCT Pub. Date: Jan. 21, 1993

[30] Foreign Application Priority Data

Jul. 1, 1991 [FR] France ................................ 9108177

[51] Int. Cl.⁶ .................................................. A61B 17/43
[52] U.S. Cl. ............................ 435/240.2; 600/35; 600/33; 128/738; 436/65; 436/906
[58] Field of Search ..................... 600/33, 34, 35; 435/240.2, 240.26, 975; 800/DIG. 6; 935/99, 107; 436/806, 906, 65

[56] References Cited

U.S. PATENT DOCUMENTS 5,084,004  1/1992  Ranoux .................................... 600/34

*Primary Examiner*—Jacqueline M. Stone
*Assistant Examiner*—Bruce R. Campell
*Attorney, Agent, or Firm*—Young & Thompson

[57] ABSTRACT

A fertilization method wherein an oocyte puncture is performed and one or more oocytes are inserted into a container containing a culture medium having no added air or $CO_2$ and intended for the fertilization and culture of the oocyte(s), as well as spermatozoa, whereafter the container is sealed and inserted into the vagina or uterus to allow fertilization of the oocyte(s) and culture of the embryo(s). The method is characterized in that it is performed without stimulating the cycle, with LH supervision by means of blood assays, and by programming the oocyte puncture according to the LH value. The container may be kept at a temperature of approximately 37° C. for 2 to 6 hours for maturation before being inserted into the vagina.

20 Claims, No Drawings

SPONTANEOUS CYCLE FERTILIZATION METHOD

BACKGROUND OF THE INVENTION

Since the birth in 1978 of Louise BROWN, the first child born as a result of in vitro fertilization, few major changes have taken place in the in vitro fertilization method.

Ovarian stimulation is now conventionally practiced on account of the ease with which oocyte retrieval can be programmed. The different ovarian stimulation procedures, clomiphene citrate - hMG, hMG alone, FSH - hMG and, more recently, the agonists of LH-RH associated with hMG, have considerably increased the number of oocytes obtained per retrieval (from 2.5 to 3.5 on average to 8 to 10 at the present time). This increase in the number of oocytes obtained has led to a larger number of embryos. In view of the risk of a multiple pregnancy caused by the transfer of more than three embryos, most assisted reproduction centers have acquired freezing apparatus to preserve the embryos and permit their secondary transfer replacement. Such stimulatory procedures are very expensive owing to the quantities of hormones used and the increased number of examinations (hormone doses and ultrasonic examinations) needed in order to monitor follicle growth.

The fertilization technique per se which is conducted in a laboratory using a $CO_2$ incubator, a laminar flow hood, an inverted microscope, represents a major initial investment (see M. D. DAMEWOOD: In Vitro Fertilization:Insurance and financial considerations. Assisted Reproduction Review 1: 38, 1991). In addition the manipulation times, which are long due to the complexity of the technique, there is the need to monitor parameters such as $CO_2$, temperature and relative humidity in the incubator. This correspondingly increases the cost of the procedure. This cost, which is high, estimated at $ 6,500 per attempt in the U.S.A. and approximately 15,000 Francs in France, makes it difficult to extend and disseminate this technique.

In addition the results which, at the best fertilization centers, are always below those for natural fertilization, namely 20% pregnancy per stimulated cycle the high cost, and the risks which result directly from this type of treatment (hyperstimulation, multiple pregnancies, storage and manipulation of frozen embryos) have prompted government agencies in the so-called developed countries to take steps to curtail the extension of assisted reproduction or procreation centers. Such steps run counter, of course, to the interests of sterile couples.

The applicant's experiments in in vitro fertilization, which were launched in 1979, have made it possible to develop a new procedure, which will be described hereinafter:

I. Intravaginal culture (IVC).

Reference is made, first of all, to international application WO 87/02879 filed on 7 Nov. 1986 and published on 21 May 1987, on which was based my U.S. Pat. No. 4,902,286 and to international application WO 88/08280 filed on 2 May 1988, on which was based my U.S. Pat. No. 5,084,004 and published on 3 Nov. 1988. All the features disclosed in these two my aforesaid U.S. Patents, shall be deemed to form part of the present description.

It was observed, in the first place, that the fertilization technique per se could be considerably simplified. Thus, I demonstrated, using the "CIVETE" technique, in French, "culture intra vaginale et transfert embryonnaire" or intravaginal culture and embryo transfer, that the addition of 5% $CO_2$ enriched air was not necessary to maintain good culture conditions. However, to avoid any disturbance in the culture medium, it was necessary to fill the tube completely, without any air. Similarly, to avoid any major disturbance to the pH of the culture medium, the sperm concentration (responsible for metabolic consumption) was substantially reduced, 10,000 to 20,000 motile spermatozoa/ml, whereas the concentration is at least 50,000 mobile spermatozoa/ml in the conventional technique. This technique necessites fewer manipulations and requires no change in the culture medium.

In the conventional in-vitro fertilization technique, denuding or removal of the cumulus masa is carried out using a pipette or a needle 18 to 30 hours after insemination. This procedure necessitates considerable skill and can be traumatic for the embryo. In the IVC technique, spontaneous denuding of the embryos occurs in over 80% of cases. Such spontaneous denuding corresponds to a spontaneous detachment of the cells of the cumulus that surround the corona (see RANOUX C., AUBRIOT F. X., DUBUISSON J. B., CARDONE FOULOT H., POIROT C., CHEVALLIER O.: A new in vitro fertilization technique: intravaginal culture. Fertil Steril 49: 654, 1988 and RANOUX C., SEIBEL, M. C.: New techniques in fertilization: Intravaginal culture and microvolume straw. J In Vitro Fert "Embryo Transfer 7": 6, 1990); it reflects the quality of the culture and that of the gametes. In the event of toxicity, due either to the sterilization means (ethylene oxide), or to the faulty preparation of the instruments when removing the oocytes, a mass of dense cells of elastic appearance surrounding the embryo, which makes it necessary to extract the same in order to assess its stage of development. The embryo in the case of mechanical denuding, using a needle or a pipette, has never attained a stage of development of more than two cells, with fragments present and the cells having an irregular, asymmetrical and abnormal appearance.

The IVC technique is simple, inexpensive and requires only a small incubator and a stereoscopic microscope placed beneath a small-sized laminar flow hood. It does not necessitate any major laboratory infrastructure, in particular a $CO_2$ incubator. The IVC technique patient participation, hence is accompanied in a better psychological context than conventional IVF techniques. This technique also constitutes a physiological improvement, with fertilization taking place in the vagina at body temperature, with the thermal variations normally observed in the periovulatory period. Fertilization carried out intravaginally raises fewer ethical problems and presents a lower risk of a mix-up of gametes. Moreover, there is no risk of an incubator breakdown which is liable to jeopardize fertilization of several patients. Thanks to its simplicity and standardization, this technique does not necessitate a high level of technical training and can be reproduced easily, without the results being affected.

It has been demonstrated, moreover, that results obtained using the IVC technique, were equivalent to those for conventional in-vitro fertilization, 15% births being obtained per retrieval.

II. Natural cycle with programming of retrieval by hCG injection.

The ovarian stimulation experiment, which is based on several years of work, with the different procedures mentioned above, has not enabled any significant difference between these procedures to be observed in respect of birth percentages per attempt. These rates, even in the best teams, are still between 10 and 15%. This was one of the main reasons that prompted us to revert to the natural cycle.

Another of these reasons was the progress achieved since the first "test-tube baby".

When the first natural cycle attempts were made, follicle growth was monitored by urine testing for estradiol (E 2) and LH, without ultrasonographic verification, whence the lack of accuracy regarding oocyte maturity and the optimal time for oocyte retrieval. Ultrasonographic scanning, in association with the advent of quick assaying the amounts of hormones present in the blood stream, for estradiol and LH, has made for greater accuracy in determining ovulation. The use of hCG in the stimulated cycles has permitted programming of follicle puncture 34 to 36 hours after the injection, thus avoiding oocyte retrieval at just any time of the day or night.

Finally, the advent of new methods of retrieval, coelioscopy being replaced by ultrasonographic scanning, more recently practiced vaginally using a vaginal probe, has permitted major technical progress. Such retrieval, with ultrasonographic scanning, does not generally necessitate anaesthesia and obviates the need for a surgical infrastructure. Use of such advances has made it possible to develop a simplified natural cycle procedure with retrieval programming using human chorionic gonadotropin hCG (see FOULOT H., RANOUX C., DUBUISSON JB., RAMBAUD AUBRIOT FX., POIROT C.: In vitro fertilization without ovarian stimulation: a simplified procedure applied in 80 cycles. Fertil Steril 52: 617, 1989).

Follow-up of follicle growth begins only at the 8th or 9th day of the cycle, depending on the normal length of the patient's cycle; the number of hormone tests is very limited, on average five per cycle with only two or three ultrasonographic examinations.

If the follicle size is greater than 18 mm with E2 greater than 180 mg/ml and without an LH peak, hCG is injected and the oocyte is removed 34 to 36 hours thereafter. If the diameter is greater than or equal to 18 mm and E2 greater than or equal to 180 mg/ml with the LH between 20 and 40 IU/l, the hCG is injected immediately and retrieval is carried out 24 hours after receiving of the blood test results. Finally, if the LH exceeds 40 IU/l, hCG is not injected and the retrieval is carried out the day after the test.

This simplified procedure has made it possible to obtain, in a study of 80 attempts, a pregnancy rate of 22.5% per cycle, 17.5% of these were continuing pregnancies with being delivered in good health. This procedure offers a number of advantages: monitoring of follicle growth is shortened, simple and far less costly. The retrieval of a single follicle is fast, simple and well tolerated by the patient. This technique does not necessitate anaesthesia, just simple preliminary medication. Owing to the absence of medication, shorter periods of technical operations, and a limited use of disposable instruments, the cost of the procedure is considerably reduced. As no stimulation takes place and only one oocyte is retrieved, there is no risk of hyperstimulation. The problems due to embryo freezing are obviated. The possibility of multiple pregnancies, with the attendant obstetric risk and neonatal mortality, is non-existent.

SUMMARY OF THE INVENTION

An object of the present invention is a fertilization method in which oocyte retrieval is performed and one or more of the oocytes is placed in a container containing a culture medium, without introducing air or $CO_2$, for fertilization and culture of the oocyte or oocytes, together with spermatozoa, and after closure the recipient is placed, in the vaginal cavity or in the uterus to permit the fertilization of the oocyte or oocytes and culture of the embryo or embryos, characterized in that the method is carried out without cycle stimulation through monitoring of LH and E2 by blood tests and programming of oocyte retrieval as a function of E2 after the LH value doubles.

No hCG injection is made prior to oocyte retrieval, but preferably immediately thereafter.

Preferably, in the case of 40-year old women, retrieval is programmed 34 to 36 hours after doubling of a baseline value of LH at a level less than 40 IU/l.

Preferably, in the case of young patients, when the LH value stagnates at a level less than 40 IU/l after the baseline value doubles, oocyte retrieval is programmed approximately 48 hours after detecting the doubling of the baseline value.

Preferably, maturation of the oocyte or oocytes is effected after retrieval. Such maturation is preferably preformed by maintaining the container at a temperature of approximately 37° C. for 2 to 6 hours.

According to an important advantage of the present invention, the method can be implemented with a single retrieved, fertilized oocyte.

To implement the method, there is provided a kit which includes a quick metering device for LH, an oocyte retrieval needle, a filtration unit for sperm preparation, a container for fertilization of the oocyte or oocytes and culture of the embryo or embryos with its embedded holding means. A culture medicine can be included for rinsing the follicle, preparing the sperm and maturing and fertilizing the oocyte. Each of these items in the kit is known per se.

The kit can further include a disposable speculum, a catheter for transferring the embryo or embryos and/or an hCG injection syringe.

Finally, all the items in the kit are sterilized, placed in a hermetic packing and are disposable.

According to a second aspect of the present invention, there is provided a method for fertilizing an oocyte or oocytes in vitro and the culture of an embryo or embryos wherein the following steps are carried out in the absence of $CO_2$ enriched air: filling a container with a fluid culture medium for oocytes and embryos, at least one oocyte and spermatozoa, closing the container, placing the container in the vaginal cavity or in the uterus in order to obtain fertilization and the cleavage of the fertilized oocyte or oocytes, characterized in that, before the container is placed in the vaginal cavity or in the uterus, it is maintained at a temperature of approximately 37° C. for 2 to 6 hours.

DETAILED DESCRIPTION OF THE INVENTION

In view of the simplicity and the success rates obtained in each of the procedures, an entirely ambulatory procedure has been contemplated that enables it to be performed in the office of a sterility specialist. The study covered two groups:

GROUP 1 (August 1990 to February 1991); this group included 15 patients: 11 less than 40 years of age and four over 40 years of age. 25 attempts using this in-office IVF procedure were carried out. Three patients in fact underwent three procedures, and four of them two procedures. The reasons it was decided to undertake IVF were fallopian sterility factors for nine patents, a sterility factor of masculine origin for three patients, sterility of unexplained origin for one patient and, finally, cervical factors for two patients.

What characterizes Group 1, and basically differentiates it from Group 2, is the supplementation of the luteal phase. In this group, this supplementation took the form of synthetic progesterone intramuscularly injected every day, in doses of 25 or 50 mg.

GROUP 2 (March 1991 to May 1991); this group included 16 patients, each of whom underwent one attempt, i.e., 16 attempts were performed in all. 13 attempts were carried out on patients less than 40 years of age, and on three patients over 40 years of age. In nine cases, sterility was of fallopian origin, in four cases of unexplained origin, in two cases, it was due to endometriosis and, in the last case, a male factor was responsible. In this group, supplementation of the luteal phase was carried out using hCG, as was initially the case in our spontaneous cycle study. The intramuscular injection of hCG was carried out on the day of transfer (1500 IU/l), and repeated twice more at three-day intervals.

As to the procedure the steps were practically the same in both groups. Differences occurred in Group 2, which we shall discuss below and which made it possible to develop a new spontaneous cycle procedure covered by this application.

The monitoring of follicle growth and the criteria for injecting hCG following oocyte retrieval were the same as those described previously, except in the case of the last eight attempts. The method of follicle puncture was the same, and was carried out with ultrasonographic scanning. However, improved experience in this technique made it possible to halve the average time required for the procedure, reducing it from 24 minutes for Group 1 (8 to 50 minutes) to 12 minutes for Group 2 (7 to 25 minutes).

The procedure used for CIV technique was as the procedure already described except for a modification which will be discussed below, and relates to the new spontaneous cycle procedure.

Another feature was changed: the method of holding the tube in the vagina. The diaphragm originally used was replaced by a plastic sponge. In the United States, the surfaces of the diaphragms carry a spermicidal substance, which could have adversely affected the quality of the embryo. Embryo transfer was carried out in the conventional manner, using a catheter.

RESULTS

GROUP 1. Out of the 25 attempts, 18 led to the retrieval of oocytes, two oocytes being obtained in four of the attempts. Out of these 22 oocytes, 22 embryos were obtained by intravaginal culture but only two biochemical pregnancies resulted from the transfer of these embryos. Out of the seven attempts in which no oocytes were obtained, five failures were due to a follicle being torn or ruptured during puncture, one to ovulation before puncture and, in the last case, the oocyte was not obtained after rinsing several times.

GROUP 2. From the 16 attempts, 16 oocytes were obtained; however, two of them presented a ruptured pellucid zone, and thus only 14 embryos resulted from CIV fertilization. Four pregnancies were obtained, of which three were clinical and were on going pregnancies, foetal heartbeats being detected ultrasonographically. Another result seems to be of interest: that is the percentage of embryos spontaneously denuded in Group 1 was 36% (8/22), whereas the percentage reached 86% in Group 2 (12/14), embryo stages with 4 or 5 cells being more frequent in this group, whereas, in Group 1 they comprised most often only two or three cells.

These results clearly demonstrate the superiority of the procedure used in the case of Group 2 in relation to that of Group 1. This difference is partly due to greater experience in the procedure, and to supplementation using hCG in the luteal phase. The essential element is thought, however, behind to be the novel spontaneous cycle procedure that will be described in detail below.

DESCRIPTION OF PREFERRED IN VITRO FERTILIZATION METHOD

The four pregnancies in Group 2 were obtained, in fact, from the last 8 attempts using the new procedure. The last eight attempts were carried out on eight patients, six less than 40 years of age and two over 40. The causes of sterility in four cases was of fallopian origin, in two cases of unexplained origin and, finally, in the last case, sterility was of male origin. In these eight attempts, hCG was not injected and retrieval was programmed solely on the basis of the LH values by evaluating the time of occurrence of the LH peak. The same LH values as previously used were adopted. The point in time of the first doubling of the base LH value at a level of less than 40 IU/l was considered as the starting point of the peak. The doubling of the LH level was most often obtained at the time of the morning blood test (between 8 and 10 a.m.). The retrieval was then programmed for 34 to 36 hours after the blood test, either the following day or during the evening. A blood test was then systematically performed in the afternoon (3 to 5 P.m.), this test sometimes revealing LH stagnation, at an LH value approximately the same as the morning value, and still below 40 UI/l. Analysis of these first results and the absence of pregnancies with this type of stagnation suggests that retrieval was effected prematurely. When such stagnation exists, retrieval should be postponed to the morning of the following day for better oocyte maturation.

With the exception of patients over the age of 40, owing to the major risk of ovulation before retrieval, oocyte maturation seemed to proceed more quickly. The LH value for the following metering test (generally on the morning of the following day), shows an LH value greater than 40 UI/l, thus confirming stagnation of the previous metering test result.

The experience of the applicant has shown that, if the E2 rate drops (30% from the previous value) or remains stable (10% above and below the previous value) in relation to the E2 rate when the baseline value has doubled for the first time, the retrieval must be programmed as planned for 34 to 36 hours after the first doubling of the LH value. In fact, the retrieval will be programmed as soon as three E2 metering results yield the same value after doubling of the LH base value. If the amount of E2 on the day following the presumed LH peak has increased by more than 20% above the amount when LH double in relation to the base value, the retrieval will be effected 30 to 34 hours after reaching the higher E2 quota (premature, false LH peak).

Another special feature is that of injecting the 5000 IU of hCG immediately after oocyte retrieval, with supplementation of the luteal phase using hCG taking place as described above. In view of the lack of precision as to maturity of the oocyte, a maturation phase has been added after oocyte collection. The oocyte is placed at 37° C. for 2 to 30 hours in a tube entirely filled with culture medium (Menezo B2), without air and $CO_2$.

The results reveal the quality of this type of procedure. Indeed, of the four pregnant patients, three pregnancies are on going clinical pregnancies.

one was a patient over the age of 40, treated for endometriosis;

one was a patient of under 40 (39 years and 11 months at the time of the procedure), treated for unexplained sterility;

one was a patient aged 30 with endometriosis and a male factor for which this technique had been adopted for diagnostic purposes, in order to determine whether fusion of the two gametes was possible. This patient had undergone insemination by a donor prior to this attempt in view of the severity of the male factor.

Finally, one patient aged 32, treated for sterility of an unexplained origin, had an abortive pregnancy. Retrieval seems to have been carried out prematurely. Analysis of the other four cases reveals the following:

In one of the patients, aged 38 and having fallopian problems, a very severe associated male factor was responsible for the obtaining of an embryo with two irregular PN's, which was transferred although there was practically no likelihood of success (the laws of Massachusetts make it compulsory to transfer any embryo obtained for assisted procreation).

In another patient, aged 32, an embryo of very fine quality was obtained at the six-cell stage, but the transfer, which was extremely difficult and traumatic (despite the injection of VALIUM, VERSED and a local anaesthetic) was probably responsible for failure.

In the case of the third patient, aged 40, presenting a fallopian factor, the embryo obtained was not of good quality, having asymmetrical, irregular blastomeres, with the presence of residual bodies.

Finally, in the case of the last patient, aged 35, having a fallopian factor, an embryo with three cells was obtained with premature oocyte retrieval.

CONCLUSIONS

Preliminary spontaneous cycle experiments with programming of retrieval by injecting 5000 IU of hCG revealed excessively low pregnancy rates, showing an incipient LH peak (doubling of the baseline level, with LH<40 IU/l). In theory hCG was injected at an unsuitable moment and, as a result, it affected the maturity of the oocyte. The applicant's experience as regards retrieval at the LH peak, large variations in the amount of E2, ranging from 120 to 350 mg/ml, were observed at the time of the LH peak, has confirmed this point. It was also observed that the follicle was very fragile and ruptured at the time of retrieval. These two observations prompted me to cease injecting hCG before retrieval in order to have the benefit of a completely natural cycle.

On the other hand, the injection of the 5000 IU of hCG immediately after retrieval appears to be of fundamental importance for supplementing the luteal phase. Indeed, one of the problems with IVF, which can explain the low success rates achieved, seems to be the lack of synchronism between the growth of the embryo and the growth of the endometrium. The embryo under optimum culture conditions may possibly develop more quickly than is natural. The opposite would be observed in the case of the endometrium, the maturation of which depends on the hormonal secretions of the granulosa cells. The potential of the granulosa cells can be reduced in the course of retrieval owing to cells being torn off during aspiration of the follicular fluid and the different follicle rinsing steps. Restoration of synchronism was contemplated by storing the embryo for a short period, 24 to 36 hours prior to its transfer, at temperatures below 37° C. (American Fertility Society, 1990, P. 38), or by storing the oocyte at 4° C. in an egg yolk based, cryoprotective culture medium for 24 hours prior to insemination. In fact the simplest method is perhaps the one which was adopted, i.e. injecting the hCG just after retrieval. The hCG will thus stimulate the granulosa cells and increase the amount of progesterone in the blood, which will promote the maturation of the endometrium as well as its receptivity with a view to embryo implantation. The injection of hCG should be postponed until the time of insemination if maturation of the oocyte exceeds 10 hours.

The essential element for the purpose of programming retrieval appears to be that of monitoring the evolution of the amount of LH in the blood. To program oocyte retrieval on the basis of the results of two daily blood tests for LH may seem to be inaccurate and inefficient. However, the results obtained for the eight attempts demonstrate the contrary, both as regards the number of oocytes collected (8/8) and the number of embryos obtained (8/8). This new procedure on the basis of two blood tests for E2 on the same day appears to give results that are equivalent or better than those for retrieval after injection of hCG.

The essential element resides in obtaining a reading of LH above 40 IU/l. Once such an amount has been obtained, it is possible to effect retrieval 24 hours after the blood test and possibly postpone the time of a retrieval which had been programmed on the basis of the first readings of the amount of LH. The addition of an oocyte maturation phase at 37° C. without $CO_2$ enriched air makes it possible to perfect oocyte quality.

The combination of the natural cycle with retrieval of a single oocyte, with ultrasonographic scanning, and its fertilization using the CIV technique has made it possible, for the first time, to carry out in vitro fertilization in the office of a sterility specialist. This technique, which is wholly performed on an ambulatory basis, necessitates neither an operating room anaesthesia, or the use of any complex technical facilities. The instruments used are simple: stereoscopic microscopes, a small laminar flow hood, and a small capacity non-$CO_2$ 37° C. incubator. All this equipment can easily be stored in an office and will not take up more than 2.3 sq.m. of floor space. The small items of equipment used are: a retrieval needle, syringes, Petri dishes, sperm preparation tubes, a tube or container for CIV with its embedded holding means (as well as, possibly, a plastic speculum, compresses, plastic forceps and a sterile bag to cover the vaginal probe) and a culture medium for rinsing the follicle, for washing the sperm, and for maturing and fertilizing the oocyte all these instruments are sterilized with gamma rays and are individually packaged in cellophane bags and disposable. The selection of this type of equipment necessitates considerable attention and experience in order to preclude an risk of toxicity and to obtain the most suitable equipment for this type of procedure. That is why I had the idea of putting together a selection of this optimum equipment in the form of an in vitro fertilization kit.

In addition to the small items of equipment already mentioned could be added a filtration unit for sperm preparation that I have developed, as well as a quick metering device for LH, known per se, together with the hCG ampoules used to supplement the luteal phase. As a minimum, the kit will thus comprise a quick metering device for LH, an oocyte retrieval needle and a container for maturation of the oocytes according to the IVC technique, and a container for fertilization of the said oocytes, or possibly a container for maturation and fertilization of the oocytes. According to the technique described in my international patent application WO 88/08280 filed on 2 May 1988, on which was based my U.S. Pat. No. 4,902,286 the container can be at least partly biodegradable, the contents of my U.S. Patent being incorporated in the present application by way of reference.

The kit represents considerable time and energy savings and, for the practitioner using this kind of procedure, it would guarantee the procedure is carried out under optimum conditions.

The cost of this procedure is considerably reduced, thus making IVF accessible to a larger number of sterile couples. The association of the natural cycle and CIV represents a far more physiological solution and does not pose the same ethical problems as the conventional technique. The advantages of this procedure, already mentioned, combined with results which, while admittedly preliminary, are very satisfactory, make it a highly recommendable technique for the treatment of sterility. This procedure will no longer be used solely as a last resort for a sterile couple but as the first examination to conducted on this couple in order to evaluate the fertilizing power of the gametes with certainty. This will make it possible to dispense with long, highly expensive sterility check-ups for all the couples. Such check-ups will now only have to be carried out in cases where the is no fusion of the gametes in the course of the procedure, thus making it possible to devote more money to the real problems of sterility.

This natural cycle can also be combined with the fertilization technique using a French straw that has already been developed and described in my U.S. Pat. No. 5,084,004. The ultimate simplification of IVF will be achieved with the use of a biodegradable French straw. The procedure will not then necessitate embryo transfer and the only human technical intervention will be that of preparing and bring together the gametes (oocyte and spermatozoa) for fertilization that is in effect conducted in vivo.

The only drawback of this procedure may be the lack of long term programming (over 24 hours) of oocyte retrieval. For this purpose, there has been developed a new procedure that uses progesterone. The effects of progesterone on LH are much debated, some considering that it causes the LH peak to occur, others that it inhibits in the LH peak.

In fact, it has been observed that the action of progesterone on the LH peak depends on the dose used and when it is administered. The experiment, on only one volunteer, of vaginally administered progesterone in a periovulatory period at a dose of 50 mg every 12 hours combined of the total disappearance of the LH peak for over 48 hours. The progesterone was administered when the estradiol level attained 150 mg/ml, that is to say a few hours before the occurrence of the LH peak. It was believed that this inhibition occurred under the control of the pituitary gland. However, an unexpected result was the gradual decrease in the amount of estradiol. This decrease would thus seem to indicate that progesterone does not act solely, at this dose, as an LH inhibitor, but also as an FSH inhibitor. The addition of natural FSH, in a dose of two to six ampoules, one to two hours after the administration of progesterone and observing the same dosage every 12 hours should prove necessary in order to maintain the increase in the estradiol levels, achieve complete maturation of the oocyte and avoid premature involution of the granulosa cells, which would be detrimental to the quality of the oocyte. This injection of FSH could also find an application in a spontaneous cycle without LH blocking by progression (sic), in order to achieve complete maturation of the oocyte in case retrieval has to be programmed prematurely for administrative reasons. Thus, two to six ampoules of FSH (150 to 450 IU) would be injected when the initial doubling of the baseline level of LH was observed and immediately upon receipt of the blood test results, with oocyte retrieval occurring 34 to 36 hours after the blood test. This procedure would be of interest in the case of patients over the age of 40 with the stagnation of LH.

I claim:

1. In an in vitro fertilization method, for human beings, in which one or more oocytes are retrieved, and the one or more oocytes and spermatozoa are introduced into culture medium in a container; the container is closed substantially without the introduction of $CO_2$ enriched air and is placed in the vaginal cavity or the uterus for fertilization and culture or culture of the one or more oocytes; estradiol (E2) and the LH measured by means of blood tests; the improvement comprising effecting oocyte retrieval without cycle stimulation or injecting chorionic gonadotropin by monitoring E2 levels after the measured LH level is double the baseline LH value, and in response to (i) a first measured LH level which is double the baseline LH value and (ii) a subsequent drop of 30% of the E2 level or relative stability of the E2 level, defined as a change less than about 10% of the previously measured E2 level, performing oocyte retrieval 34 to 36 hours after said first measured LH level.

2. In an in vitro fertilization method, for human beings, in which one or more oocytes are retrieved, and the one or more oocytes and spermatozoa are introduced into culture medium in a container; the container is closed substantially without the introduction of $CO_2$ enriched air and is placed in the vaginal cavity or the uterus for fertilization and culture or culture of the one or more oocytes; estradiol (E2) and the LH measured by means of blood tests; the improvement comprising effecting oocyte retrieval without cycle stimulation or injecting chorionic gonadotropin by monitoring E2 levels once the measured LH level is double the baseline LH value, and in response to (i) a first measured LH level double the LH baseline value and (ii) a subsequent 20% increase of the E2 level, performing oocyte retrieval 30 to 34 hours after the measured E2 level with a subsequent 20% increase.

3. In an in vitro fertilization method, for human beings, in which one or more oocytes are retrieved, and the one or more oocytes and spermatozoa are introduced into culture medium in a container; the container is closed substantially without the introduction of $CO_2$ enriched air and is placed in the vaginal cavity or the uterus for fertilization and culture or culture of the one or more oocytes; estradiol (E2) and the LH measured by means of blood tests; the improvement comprising effecting oocyte retrieval without cycle stimulation or injecting chorionic gonadotropin by monitoring E2 levels after the measured LH level is double the baseline LH value, and in response to (i) a first measured LH level double the LH baseline value and (ii) subsequent successive measured E2 levels with relative stability, defined as a change less than about 10% of the previous level, performing oocyte retrieval.

4. Fertilization method according to claim 1, 2 or 3, wherein the blood tests for E2 and LH levels are carried out twice a day, once between about 8 a.m. and about 10 a.m. and once between about 3 p.m. and about 5 p.m.

5. Fertilization method according to claim 1, 2 or 3, wherein maturation of the one or more oocytes is effected after retrieval and prior to bringing the one or more oocytes into contact with spermatozoa.

6. Method according to claim 5, wherein the maturation step comprises maintaining the one or more oocytes at a temperature of approximately 37° for two to six hours without CO2 enriched air.

7. Method according to claim 1, 2 or 3, wherein a single oocyte is retrieved and fertilized.

8. Fertilization method according to claim 1, 2 or 3 wherein hCG is administered as soon as practicable after oocyte retrieval.

9. A fertilization method according to claim 1, 2 or 3, further comprising the step of providing a kit comprising a quick metering device for LH, an oocyte retrieval needle, a filtration unit for sperm preparation, a container for fertilization of the one or more oocytes and culture of one or more embryos, holding means for the fertilization container, and culture media for rinsing follicles, washing spermatozoa and fertilization of the oocyte.

10. Fertilization method according to claim 9, wherein the kit further comprises a container for maturation of the one or more oocytes, and culture medium for maturation of the one or more oocytes.

11. Fertilization method according to claim 10, wherein the container is at least partially biodegradable.

12. Fertilization method according to claim 9, wherein the kit further comprises a disposable speculum.

13. Fertilization method according to claim 9, wherein the kit further comprises a catheter for transfer of the embryo or embryos.

14. Fertilization method according to claim 9, wherein the kit further comprises a chorionic gonadotropin syringe, oocyte retrieval syringes and follicle rinsing syringes.

15. Fertilization method according to claim 9, wherein the kit further comprises Petri dishes, compresses and a plastic member covering the oocyte retrieval probe.

16. Fertilization method according to claim 9, wherein all contents of the kit are sterilized, hermetically packed and disposable.

17. Fertilization method according to claim 1, 2 or 3, wherein the blood tests are carried out twice a day.

18. Fertilization method according to claim 1, wherein the blood tests for E2 and LH levels are carried out twice a day, once between about 8 a.m. and about 10 a.m. and once between about 3 p.m. and about 5 p.m.

19. Fertilization method according to claim 2, wherein the blood tests for E2 and LH levels are carried out twice a day, once between about 8 a.m. and about 10 a.m. and once between about 3 p.m. and about 5 p.m.

20. Fertilization method according to claim 3, wherein the blood tests for E2 and LH levels are carried out twice a day, once between about 8 a.m. and about 10 a.m. and once between about 3 p.m. and about 5 p.m.

* * * * *